US00PP10020P

United States Patent [19]

Lemon

[11] Patent Number: Plant 10,020

[45] Date of Patent: Sep. 2, 1997

[54] VARIETY OF GERANIUM PLANT NAMED 'LUCILLE'

[75] Inventor: David Lemon, Lompoc, Calif.

[73] Assignee: John Bodger and Sons Company, South El Monte, Calif.

[21] Appl. No.: 571,167

[22] Filed: Dec. 12, 1995

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Fulwider, Patton, Lee & Utecht, LLP

[57] ABSTRACT

The cultivar is characterized by its new salmon scarlet color and very dark zone. Its compact, controlled growth habit and prolific blooms provide for superb cuttings and performs equally well in hanging baskets or in a ground bed. The blooms are heat tolerant.

1 Drawing Sheet

BACKGROUND OF THE NEW PLANT

The present invention comprises a new and distinct cultivar of *Pelargonium×hortorum* known by the varietal name Lucille (Oglevee No. 9058, Bodger No. 9GM 87-1). The new variety was discovered in a selective breeding program by David Lemon at Bodger Seeds, Ltd., Lompoc, Calif. The new variety is a selection from the crossing of Pink Floral Cascade (unpatented)×Bodger No. 8GM 189-1. Pink Floral Cascade is distinguished from Lucille primarily by its smaller, lighter salmon flowers and by the fact that it is a much more open, less branched plant.

The New cultivar was first asexually reproduced by cuttings at Oglevell Ltd., Connellsville, Pa., and has been repeatedly asexually reproduced by cuttings at Oglevee Lts. in Connellsville, Pa. It has been found to retain its distinctive characteristics through successive progagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200 to 250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Feb. 15, 1995 and flowered Apr. 1, 1995 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium×hortorum.*

Form: Semi-dwarf, free basal branching; uniform mound.

*Height.*—16.0–17.0 cm from the media surface.

*Growth.*—Self-branching, mound habit with some cascading growth.

*Strength.*—Free standing; free and early flowering.

Foliage: Very dark zone present, stalked leaf attachment.

Leaves:

*Size.*—7.5–8.5 cm across.

*Shape.*—Reniform; cordate base.

*Margin.*—Crenate lobed.

*Texture.*—Lightly pubescent, slightly reflective.

*Color.*—Top: Green Group 137C; Zone: Grayed/Purple Group 183A; Bottom: Yellow/green Group 147B.

*Ribs and veins.*—Palmate venation: Color: Yellow/Green group 147D.

Petioles:

*Length.*—6.0–9.0 cm.

*Color.*—Yellow/green group 146B.

Stem:

*Color.*—Yellow/green group 146B.

*Internodes.*—0.8–1.8 cm in length.

THE BUD

Shape: Upright; hemispherical cluster, elliptical floret 0.8–0.9 cm in length at first hint of color.

Size: 2.5–3.3 cm across.

INFLORESCENCE

Blooming habit: Upright, continuous, floriferous blooming.

Size: 5.3–7.2 cm across.

Borne: Florets on pedicel; pedicel on peduncle; 4.2–6.3 cm above foliage.

Florets:

*Form.*—Flat to slightly cupped.

*Number.*—About 18 florets per inflorescence.

*Color.*—Top: Red Group 43B; Bottom: Red Group 41C; Eye: None Present.

*Petals.*—9–15 in number; separate, not united; margin entire; obovate, flat to slightly cupped.

*Size.*—1.7–2.0 cm in length; 1.2–1.6 cm in width.

*Texture and appearance.*—Smooth and satiny. Appearance from a distance is clear, velvety salmon scarlet bloom above medium green foliage with a very prominent dark zone.

Petaloids:

*Quanity.*—0 to 4.

*Shape.*—Narrow, elongated, twisted.

*Color.*—Top: Red Group 43B; Bottom: Red Group 41C.

Pedicel:
*Length.*—1.8–2.7 cm.
*Color.*—Yellow/green group 146B.
Peduncle: Arises from node opposite leaf petiole.
*Length.*—11.0–13.0 cm in length.
*Color.*—Yellow/Green Group 146B.
Persistence:
*Disease resistance.*—Not known.
*Lasting quality.*—Very continuous blooming, heat tolerant.

REPRODUCTIVE ORGANS

Stamens:
*Anthers.*—1.8–2.0 mm in length.
*Filaments.*—6.0–8.0 mm in length; white or slightly pink.
*Pollen.*—Golden Brown.
Pistils:
*Number.*—One.
*Length.*—2.0 mm.
*Stigma.*—5–6 parted. red/purple in color.
*Style.*—1.8–2.0 mm, pink in color.
Ovaries: Superior; pale green in color, 3.0 mm in length, 1.8 mm across.

Fruit: None observed.

GENERAL CHARACTERISTICS

Lucille brings a new salmon scarlet color to the range of pink, light pink, red, light salmon and white geranium varieties already in the market place. The very dark zone is more prominent than the zoning in the other varieties currently available. Similar to the other varieties, Lucille produces many small flower clusters that create a large continuous bouquet above medium green foliage with a very dark zone. Growth habit is a neat mound which is suitable for container, ground beds or hanging basket use. Cutting production is very good being equal to or better than the current variety Elizabeth (U.S. Plant Pat. No. 8.192). Elizabeth is distinguished from Lucille by its red flowers and medium dark leaves. Lucille, on the other hand, has dark coral flowers, and medium green leaves.

I claim:

1. A new and distinct variety of geranium plant, substantially as shown and described.

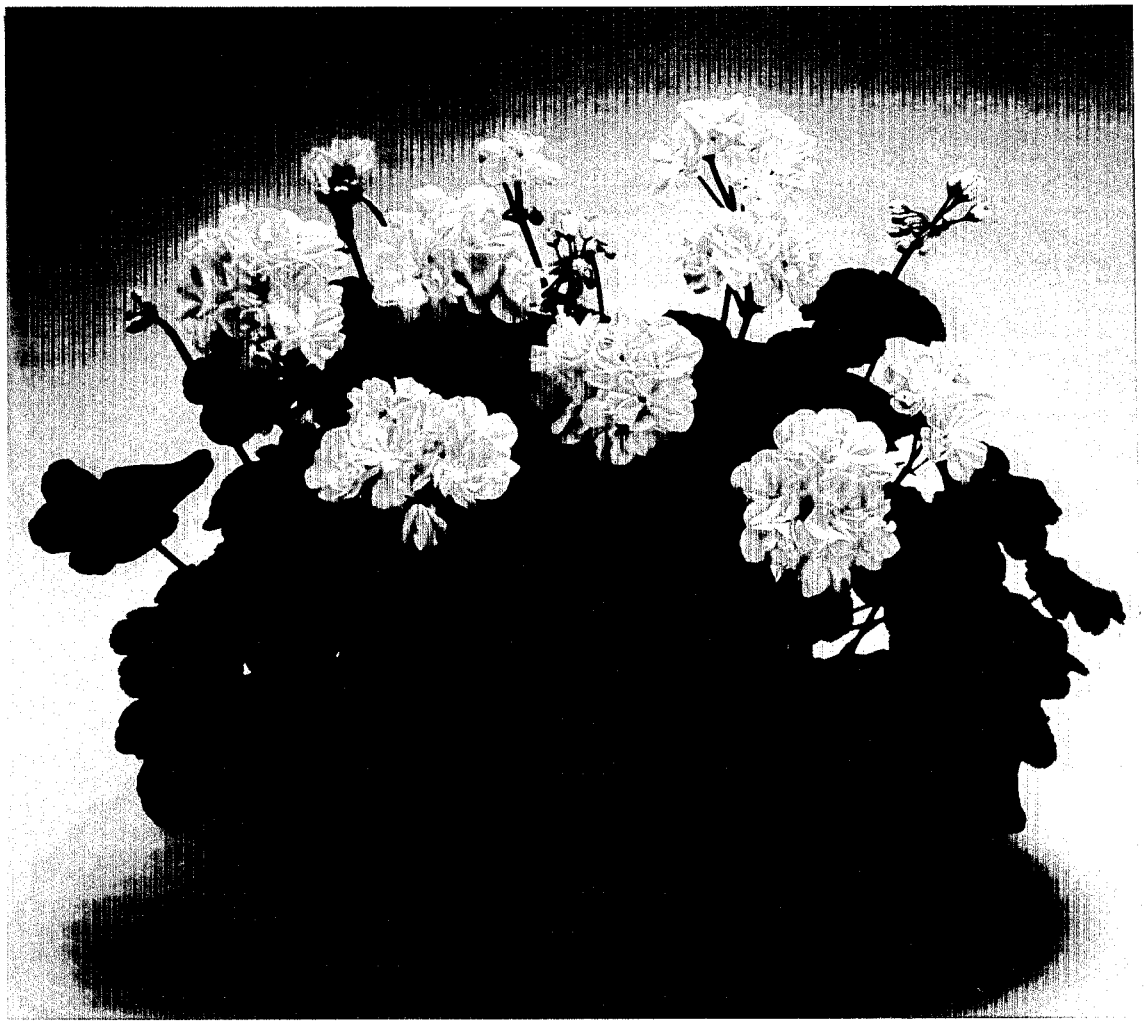

* * * * *